US 6,669,090 B2

(12) United States Patent
Eilersen

(10) Patent No.: US 6,669,090 B2
(45) Date of Patent: Dec. 30, 2003

(54) ELECTRONIC MARKING OF A MEDICATION CARTRIDGE

(75) Inventor: Michael Eilersen, Hvidovre (DK)

(73) Assignee: Novo Nordick A/S, Bagsvaerd (DK)

( * ) Notice: Subject to any disclaimer, the term of this patent is extended or adjusted under 35 U.S.C. 154(b) by 0 days.

(21) Appl. No.: 09/925,995

(22) Filed: Aug. 9, 2001

(65) Prior Publication Data

US 2002/0022821 A1 Feb. 21, 2002

Related U.S. Application Data

(60) Provisional application No. 60/229,078, filed on Aug. 30, 2000.

(30) Foreign Application Priority Data

Aug. 10, 2000 (DK) ........................................ 2000 01199

(51) Int. Cl.[7] ............................................... G06F 19/06
(52) U.S. Cl. .............................. 235/462.03; 235/472.01
(58) Field of Search ........................ 235/472.01, 462.03

(56) References Cited

U.S. PATENT DOCUMENTS

| 3,700,862 | A | 10/1972 | Snook et al. |
|---|---|---|---|
| 4,449,042 | A | 5/1984 | Hampson et al. |
| 4,476,381 | A | 10/1984 | Rubin |
| 4,693,574 | A | 9/1987 | Ohnuki et al. |
| 4,978,335 | A | 12/1990 | Arthur, III |
| 5,394,206 | A | 2/1995 | Cocca |
| 5,895,369 | A | 4/1999 | Flower |
| 5,902,990 | A | 5/1999 | Stewart |
| 5,954,700 | A | 9/1999 | Kovelman |
| 6,110,152 | A | 8/2000 | Kovelman |

FOREIGN PATENT DOCUMENTS

| DE | 26 36 634 A1 | 2/1978 |
|---|---|---|
| DE | 198 14 687 C1 | 4/1998 |
| EP | 0 402 553 A1 | 11/1989 |
| GB | 2 159 007 A | 11/1985 |
| JP | 59131917 | 7/1984 |
| JP | 8118864 A | 10/1994 |
| JP | 9034361 A | 7/1995 |
| WO | WO 99/65548 | 12/1999 |
| WO | WO 01/54055 | 7/2001 |

*Primary Examiner*—Harold I. Pitts
(74) *Attorney, Agent, or Firm*—Reza Yacen, Esq.; Richard H. Bark, Esq.; Marc A. Began, Esq.

(57) ABSTRACT

The invention relates to: A method of providing an electronically readable item of information (725) on a medication cartridge (70). The invention further relates to a cartridge (70) containing an electronically readable item of information (725), a support (75) for reading the information (725) on the cartridge (70), a medication delivery device adapted to use a cartridge (70) and a support (75) according to the invention and a label (72) containing an electronically readable item of information (725). The object of the present invention is to provide an alternative method of generating an electronically readable item of information on a cartridge which method is simple and improves safety in reading. The problem is solved in that said item of information is redundantly provided (725, 726). The invention may e.g. be used in connection with medication delivery devices for self-treatment of a disease, e.g. diabetes.

11 Claims, 11 Drawing Sheets

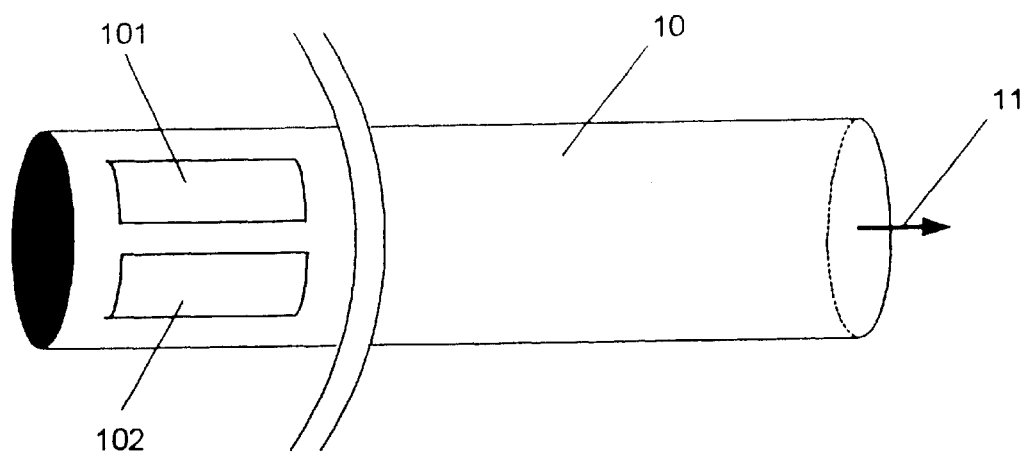
Fig. 1.a
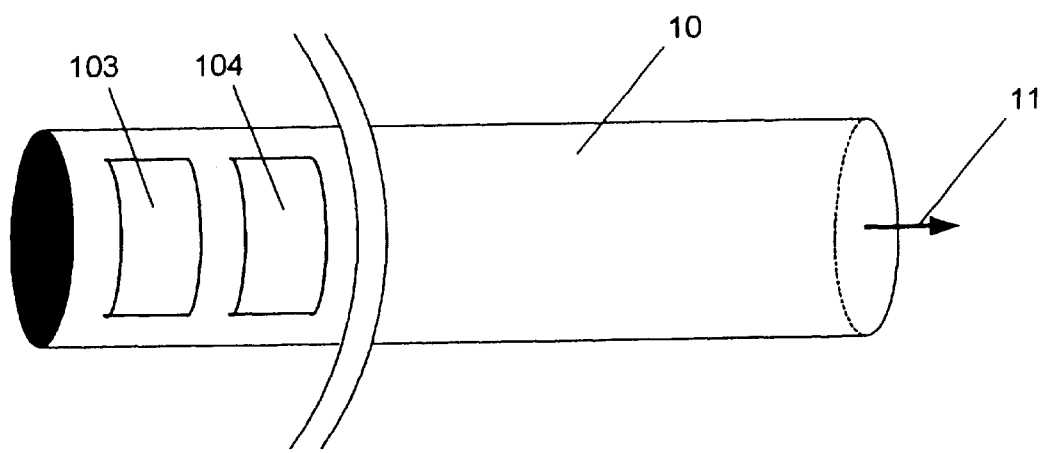
Fig. 1.b
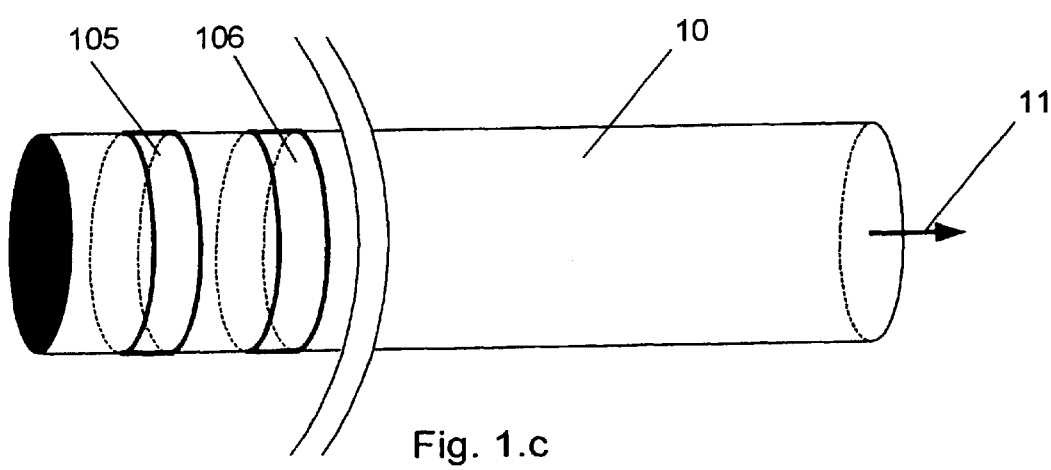
Fig. 1.c

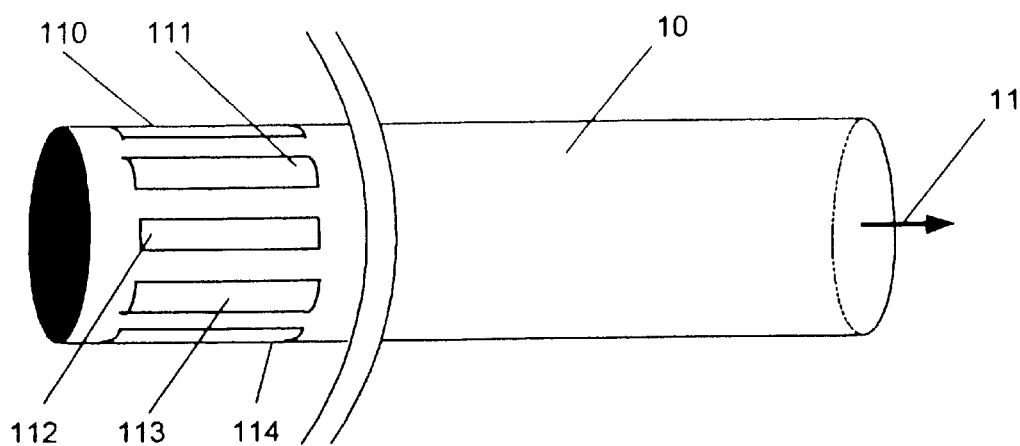
Fig. 1.d
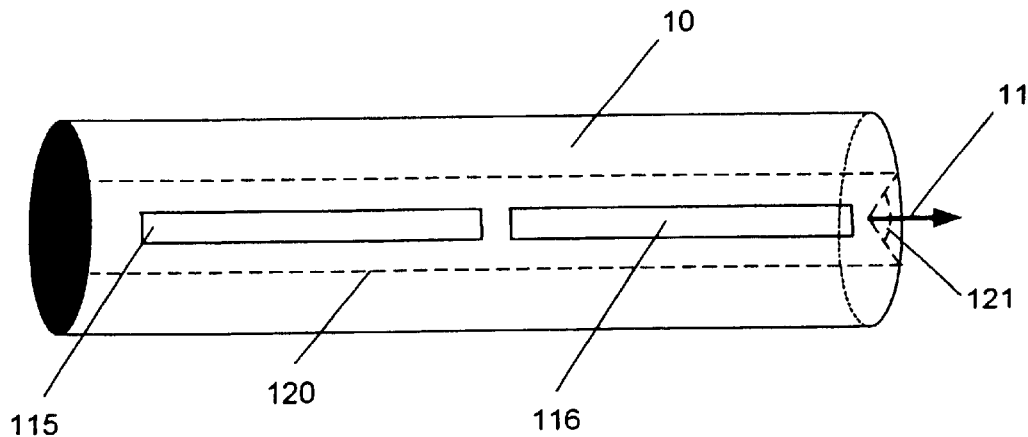
Fig. 1.e
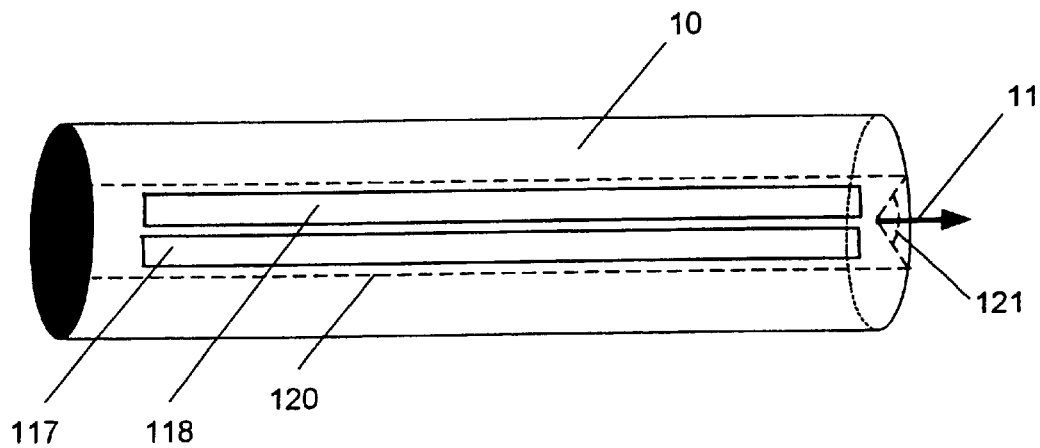
Fig. 1.f

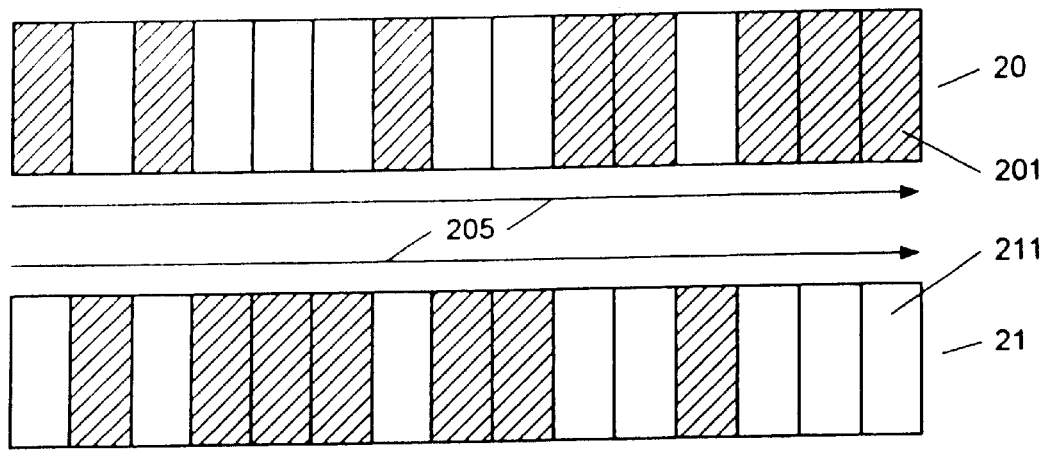
Fig. 2.a
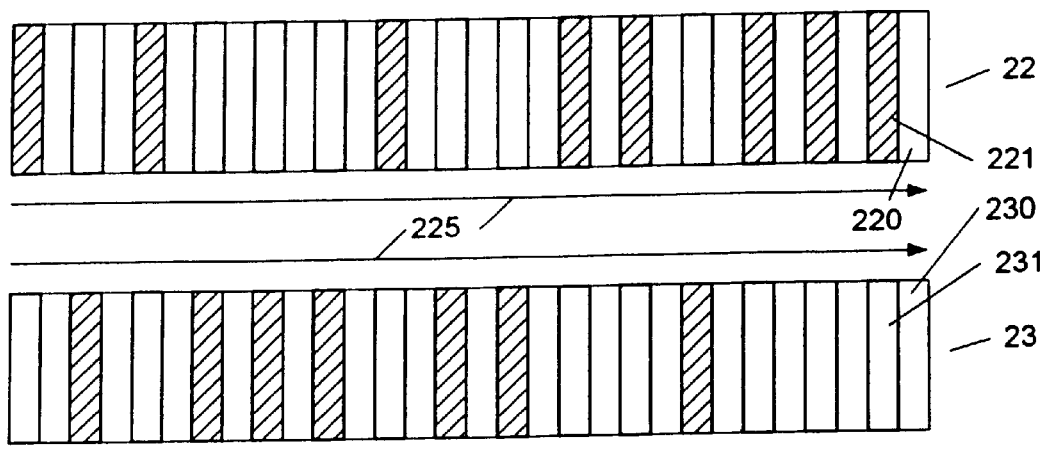
Fig. 2.b

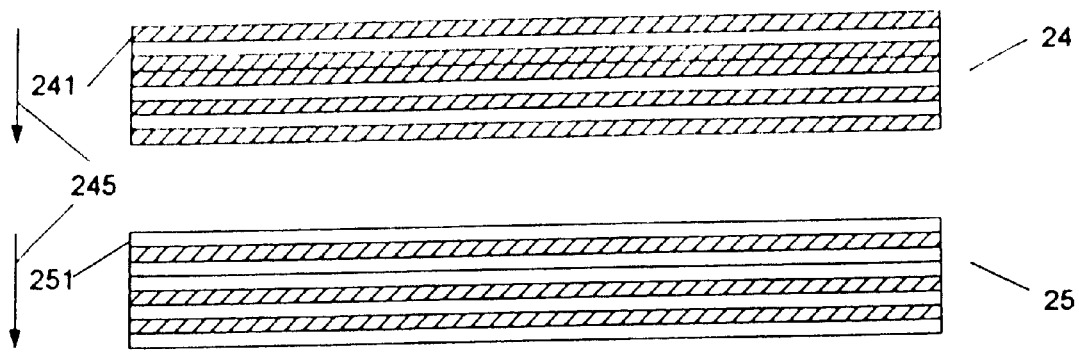
Fig. 2.c
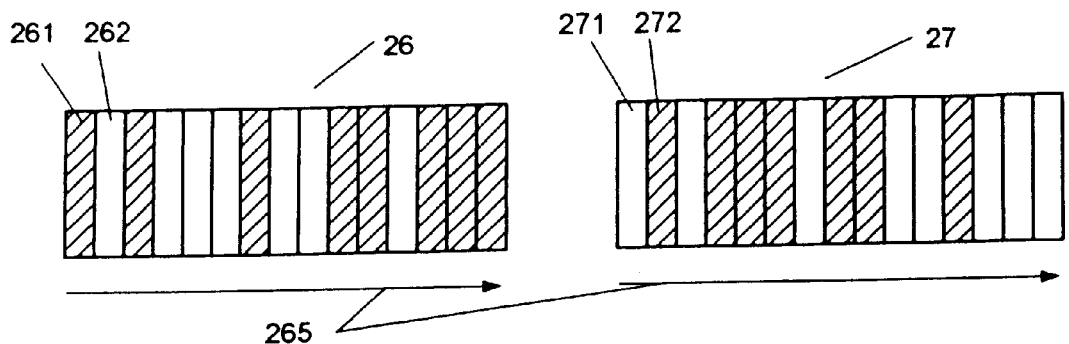
Fig. 2.d
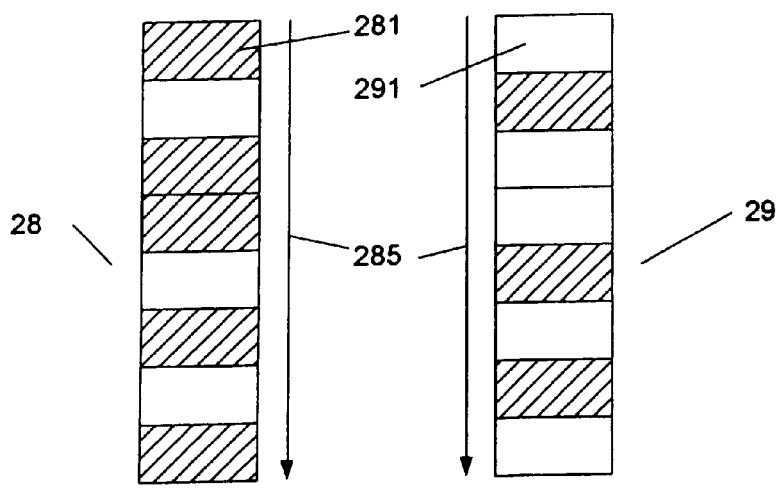
Fig. 2.e

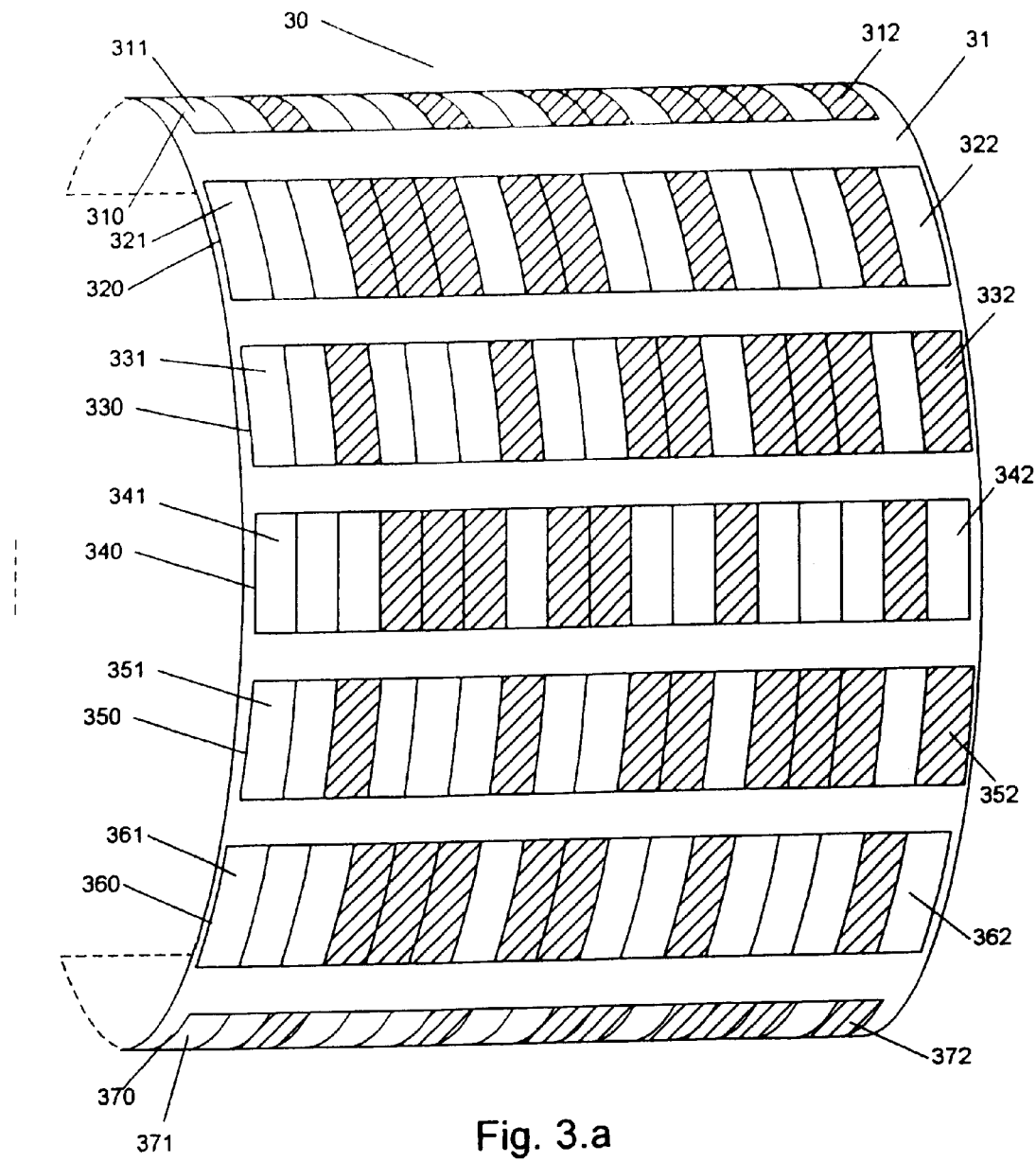
Fig. 3.a

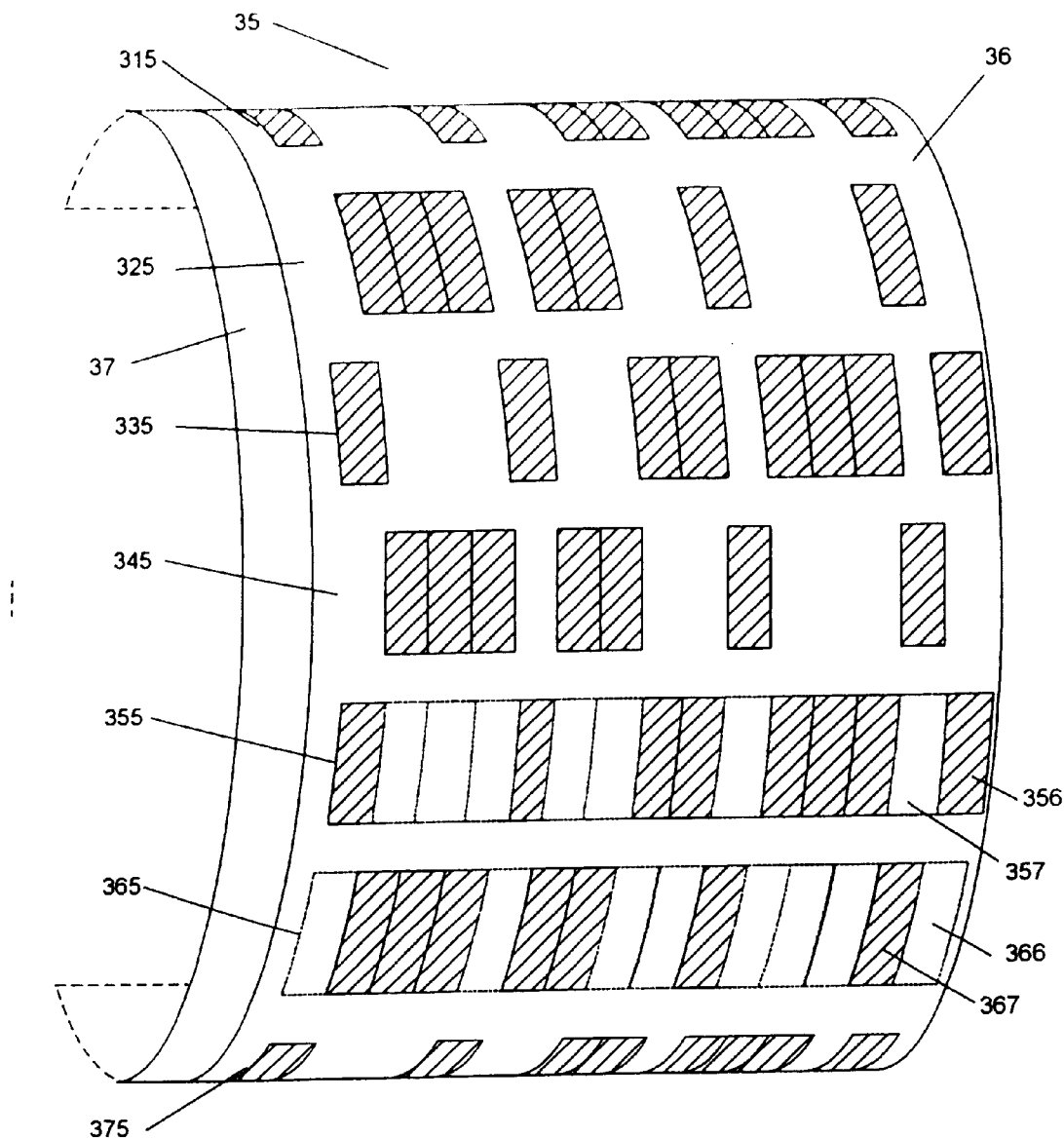
Fig. 3.b

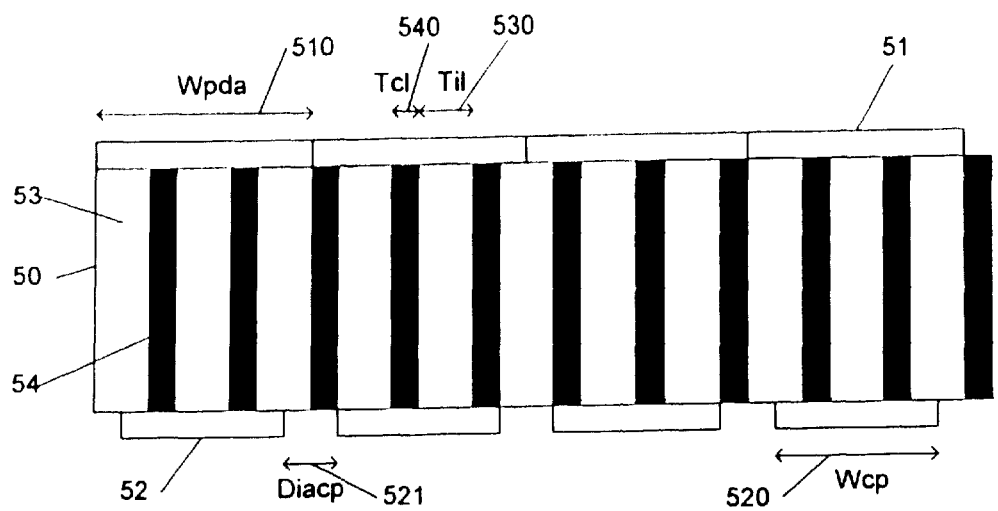
Fig. 5.a
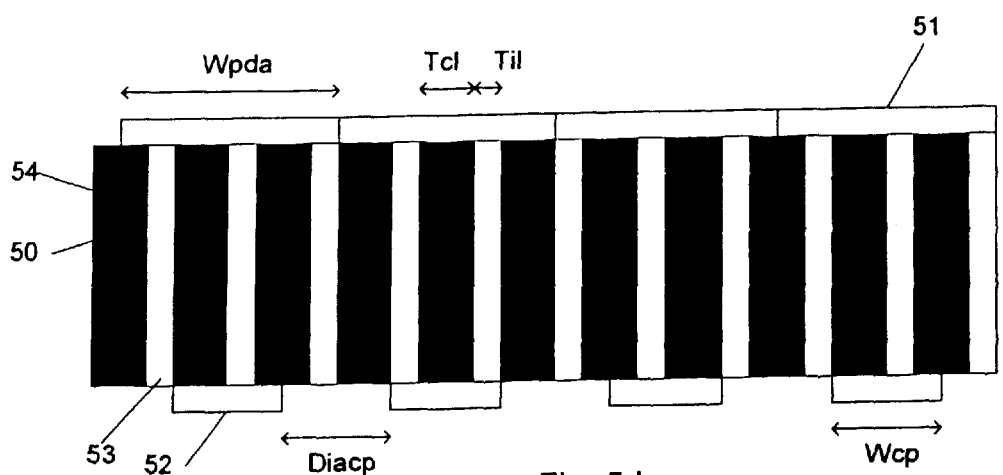
Fig. 5.b
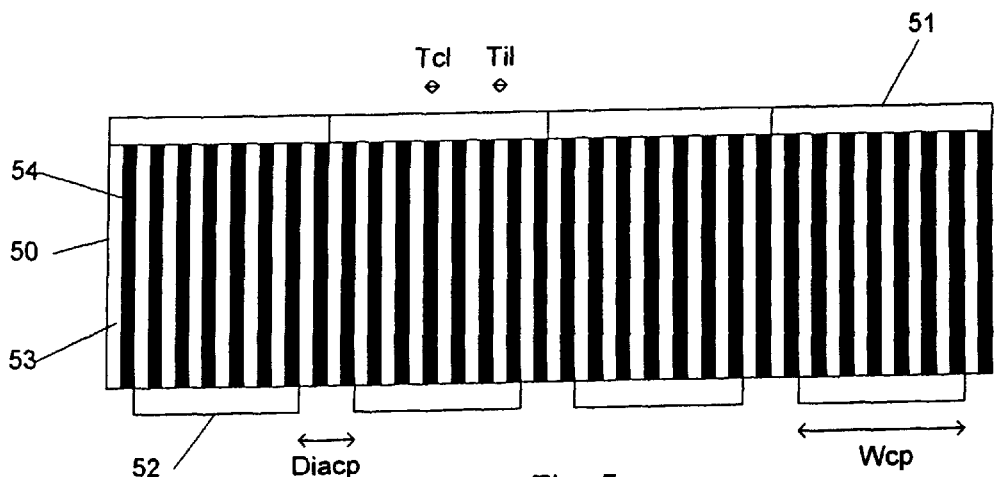
Fig. 5.c

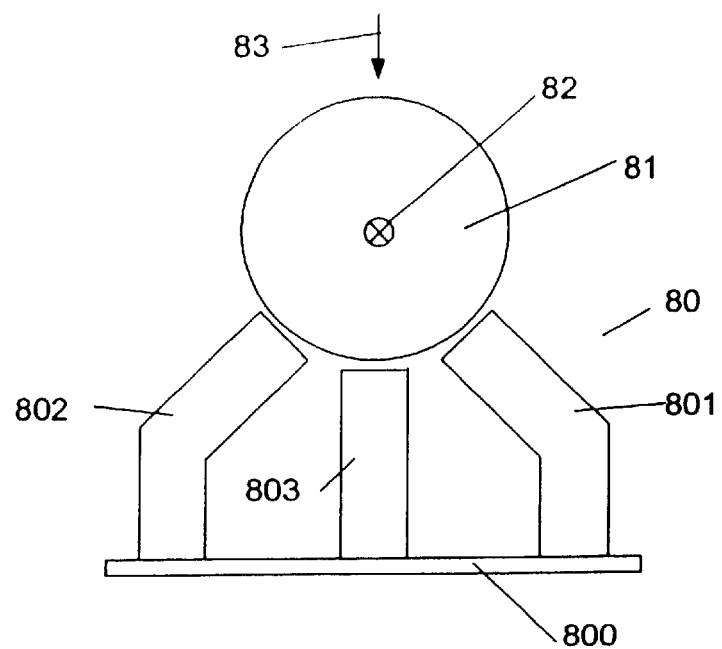
Fig. 8.a
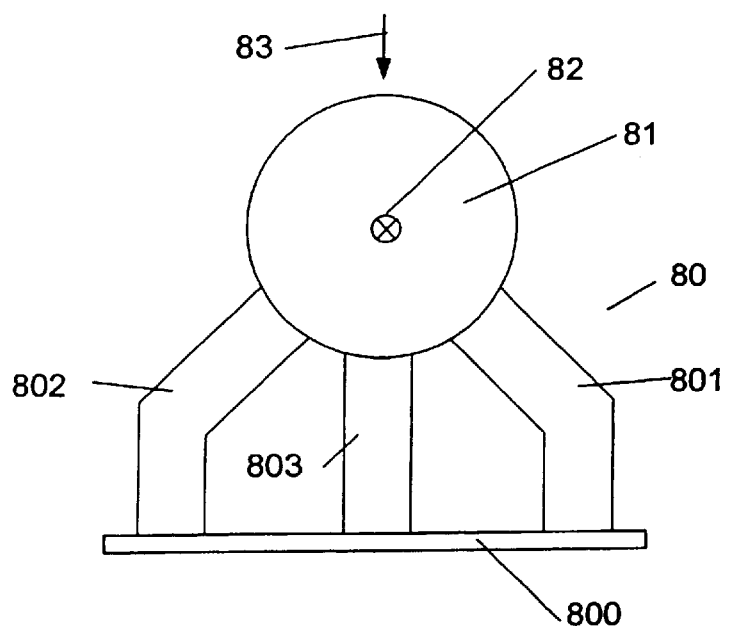
Fig. 8.b

ELECTRONIC MARKING OF A MEDICATION CARTRIDGE

CROSS-REFERENCE TO RELATED APPLICATIONS

The present application claims priority on U.S. provisional application No. 60/229,078, filed on Aug. 30, 2000.

THE TECHNICAL FIELD OF THE INVENTION

The invention relates to the electronic marking of medication cartridges or the like.

The invention relates specifically to: A method of providing an electronically readable item of information on a medication cartridge.

The invention furthermore relates to: A medication cartridge with an information-providing source containing an electronically readable item of information.

The invention furthermore relates to: A support for a medication cartridge provided with an electronically readable item of information.

The invention moreover relates to: A medication delivery device having means for processing and displaying information.

The invention moreover relates to: An information carrier with an electronically readable item of information for a medication cartridge.

DESCRIPTION OF RELATED ART

The following account of the prior art relates to one of the areas of application of the present invention, cartridges containing medication for injection, infusion or inhalation by a user.

In applications of medication delivery devices for self-treatment of a disease, e.g. diabetes, cartridges containing medication for a certain number of doses are mounted in the delivery device and exchanged with a new one when empty or when another medication is to be used according to the particular situation. It is of paramount importance that the medication used is the intended one, that it is not too old, that it has the correct concentration etc. Therefore the marking of the cartridge containing the medication has to be given special attention. To aid the user in achieving a satisfactory level of security in the use of a medication delivery device, a marking of the cartridge in addition to a traditional alphanumeric inscription has been introduced. Apart from information on the contents of the cartridge, the item of information may hold technical data on the type of cartridge, outlet dimension or other information of relevance to the medication delivery process.

U.S. Pat. No. 5,954,700 discloses a cartridge for containing a fluid and for use with an electronic delivery device that includes a cartridge housing for holding the fluid, and an information providing source. The information-providing source may be a set of wires and contacts, or contact bands that provide the predetermined information to an electronic delivery device by producing a binary code.

The possible spill of drops of the medication from the medication cartridge may typically deteriorate the readability of the optically readable or electronically readable coded information on the cartridge due to chemical reactions. This calls for a method of marking that is robust and does not allow the introduction of errors in the interpretation of the coded information in case of minor deteriorations of the code in question.

DISCLOSURE OF THE INVENTION

The problem of the prior art is to provide a method of marking a cartridge, which method is simple and safe and easily readable by electronic means.

Thus, the object of the present invention is to provide an alternative method of generating an electronically readable item of information on a cartridge which method is simple and improves safety in reading.

This is achieved according to the invention in that said item of information is redundantly provided. In this way, a very simple method is provided that may be implemented in a multitude of ways, customized to each specific application.

In the present context, the term 'cartridge' is taken to mean a container for holding a liquid or powder or other matter of a size and weight that can be handled by hand. The cartridge may e.g. be a cartridge containing medication for use with a medication delivery system for self-treatment of a disease. The medication in the cartridge may e.g. be insulin for use with a pen-type injection system for treating diabetes.

In a preferred embodiment said item of information is provided at least once in a binary true and inverted form.

In the present context, the term 'redundantly provided in a binary true and inverted form' is taken to mean that the information is provided in a way that may be directly translated to a binary representation (e.g. 100110) and that the same item of information is provided in its true (e.g. 100110) and inverted (011001) form, yielding a redundancy that may be used to check the validity of the electronically read code. I.e. if e.g. one or more of the ('should be') inverted bits equals the corresponding bits of the true representation, an error is present. This check gives a higher degree of safety in interpreting the item of information in question, which e.g. is important when the container is used for medication in connection with a person's self-treatment of a disease.

Apart from the above mentioned redundancy, each item of information (in its binary true or inverted forms) may be subject to standard error detecting measures, such as reserved bits for a parity check, a CRC (Cyclic Redundancy Check) or the like, and/or error correcting measures.

When said item of information is provided in any one of its binary forms by forming electrically insulating and electrically conducting areas corresponding to the relevant state of each bit of information in predefined positions on the surface of the cartridge, it is ensured that a very simple, flexible and inexpensive method is provided.

When said medication cartridge has an axis of rotational symmetry, it is ensured that a reading procedure that is independent of the rotational orientation of the cartridge is possible. This makes the positioning procedure of the cartridge in the medication delivery device convenient for the user in that he or she does not have to think about its correct orientation in the circumferential direction, defined as a circumference on the surface of the cartridge in a direction perpendicular to the axis of symmetry (also termed the 'radial direction'in the following).

When said electrically insulating or electrically conducting areas fully or partially circumfere said axis of symmetry, thus defining two or more information carrying areas, each containing said item of information in its binary true or inverted form, on said cartridge, it is ensured that the reading of the information may be made independent of the radial orientation of the cartridge.

When said electrically insulating or electrically conducting areas are positioned in one or more longitudinal areas stretching in the direction of said axis of symmetry, each longitudinal area covering only a fraction of the circumference of said cartridge, thus defining two or more information carrying areas, each containing said item of information in its binary true or inverted form, on said cartridge, it is ensured that information carrying areas may be evenly distributed in the radial direction of the cartridge, and thereby making the reading of the information independent or nearly independent of the radial orientation of the cartridge.

When said item of information is provided in any one of its binary forms by applying electrically insulating areas to predefined positions on an electrically conducting foil, said foil being positioned on said cartridge, it is ensured that a very simple and convenient method for adding an electronically readable item of information to a cartridge is provided, which method is well suited for mass production.

When said item of information is read by applying a voltage to said electrically conducting foil, said voltage corresponding to the supply voltage of one of the logic levels of a digital processing circuit, and by connecting each predefined position on the foil electrically with inputs to a digital processing circuit, it is ensured that a very simple, and inexpensive method is provided that may take a variety of forms, customized to each specific application. It further has the advantage that no additional components or extra, customized wiring on the cartridge is necessary in order to define and electronically read a specific item of information.

When said inputs to the digital processing circuit are provided with pull-up or pull-down circuitry according to which of the supply voltages of the logic levels of said digital processing circuit is applied to said electrically conducting foil, it is ensured that a simple and easily producible scheme is provided.

When said inputs to the digital processing circuit may be selectably provided with either pull-up or pull-down circuitry according to which of the supply voltages of the logic levels of said digital processing circuit is correspondingly selectably applied to said electrically conducting foil, said selection being controlled by said digital processing unit, it is ensured that the probability of falsely reading the item of information in question is reduced.

When the redundant information from two or more information carrying areas on the cartridge is transferred to a contact area that is connected to a processing circuit by supporting means for the cartridge, the supporting means being at least partially constituted by two or more electrically connecting supports, each comprising a number of closely spaced mutually electrically insulated conductors embedded in an electrically insulating material that stretches from one of the supporting surfaces of the cartridge to a contact area for receiving and transferring the information to said processing circuit, when said cartridge is positioned in said support, it is ensured that a flexible method of simultaneously supporting the cartridge and transferring the information from the cartridge to a contact area for further processing is introduced.

When each of said two or more electrically connecting supports is constituted by alternating layers of electrically conducting material of maximum thickness $T_{cl}$ and electrically insulating material of maximum thickness $T_{il}$, respectively, it is ensured that a method well suited for transferring a high information density is disclosed. By controlling the dimensions of the layer thicknesses and the corresponding geometries of the contact area and the information carrying areas, the information density may be controlled, i.e. by shrinking the layer thicknesses the information density may be increased.

When said alternating layers are made of elastic materials, it may be ensured that the electrically connecting supports conform to the shape of the cartridge when the cartridge is positioned in the support with a certain minimum pressure. I.e. it makes the support even more flexible and relaxes the tolerances to its conformity with the cartridge and with the contact area (e.g. pads on a printed circuit board (PCB) for connecting to a processing circuit on the PCB).

A medication cartridge with an information-providing source containing an electronically readable item of information is moreover provided by the present invention. When said item of information is redundantly provided at least once by applying electrically insulating and electrically conducting areas corresponding to the relevant state of each bit of information in predefined positions on the surface of the cartridge, it is ensured that a cartridge containing an electronically readable item of information implemented in a simple way is provided, which cartridge is well suited for being part of a system that requires a high safety in information transfer, such as e.g. a medication delivery system for self-treatment of a disease.

When said item of information is formed on a self-adhesive carrier positioned on the surface of the cartridge, it is ensured that a simple and convenient means for providing an item of information to a cartridge is provided.

In a preferred embodiment said cartridge has an axis of rotational symmetry.

In a preferred embodiment information carrying areas containing said item of information in its true and inverted forms, respectively, are positioned side by side in the direction of said axis of symmetry of said cartridge.

In a preferred embodiment information carrying areas containing said item of information in its true and inverted forms, respectively, are positioned side by side in the direction of a circumference of said axis of symmetry of said cartridge.

When information carrying areas containing said item of information in its true and inverted forms, respectively, appear alternatingly a multitude of times in a direction of a circumference of said axis of symmetry of said cartridge, it is ensured that the same item of information is provided redundantly and repeatedly, which potentially facilitates the reading process. Furthermore, when a rotational symmetry is introduced, a reading procedure that is independent of the rotational orientation of the cartridge is possible.

When said item of information is provided in any of its binary forms by applying electrically insulating areas in predefined positions on the surface of an electrically conducting foil positioned on said cartridge in such a way that an electrically insulating area is applied at those predefined positions representing one predefined binary state, and an electrically conductive area is provided at those predefined positions representing the complementary binary state, it is ensured that a simple, flexible and economic configuration for electrically transferring an item of information from a cartridge to a processing means is provided.

When said item of electronically readable information is provided on the cartridge in an optically readable form, it is ensured that the item of information included on the cartridge for being electronically read may be read also directly by a user and/or by an optical scanner.

A support for a medication cartridge provided with an electronically readable item of information is furthermore provided. When said item of information being redundantly provided at least once by forming at least two information carrying areas containing electrically insulating and electrically conducting areas corresponding to the relevant state of each bit of information in predefined positions on the surface of said cartridge, and said support for the cartridge is at least partially constituted by two or more electrically connecting supports, each comprising a number of closely spaced mutually electrically insulated conductors embedded in an electrically insulating material that stretches from one of the supporting surfaces of the cartridge to a contact area for receiving and transferring the information to a processing circuit, when said cartridge is positioned in said support, it is ensured that the item of information on the cartridge may be transferred to an electronic circuit via an 'adapter' that may be adjusted to the particular embodiment of the cartridge and the physical device which it is part of. A support of this type is further disclosed in our co-pending application "A support for a cartridge for transferring an electronically readable item of information from the cartridge to an electronic circuit".

When each of said two or more electrically connecting supports is constituted by alternating layers of electrically conducting material of maximum thickness $T_{cl}$ and electrically insulating material of maximum thickness $T_{il}$, respectively, it is ensured that a simple and flexible solution is provided. By controlling the thicknesses of the two layer types, the maximum density of information may be controlled.

When said cartridge has an axis of rotational symmetry, and said contact area consists of groups of identical and regularly spaced electrically conducting pads of width Wcp in the direction of adjacent pads, adjacent pads being separated by an electrically insulating area of width Diacp, and the following relations between said distances are fulfilled:

$$Diacp > 2*T_{cl},$$

and $$Wcp > T_{il} + T_{cl},$$

it is ensured that the electrical states of adjacent (possibly abutted) predefined positions are not transferred to the same pad (Diacp>2*$T_{cl}$), and that at least one conducting layer contacts any given pad (Wcp>$T_{il}$+$T_{cl}$).

When said cartridge has an axis of rotational symmetry, and said cartridge is provided with a multitude of rectangular, essentially parallel, identically sized information carrying areas of height Hica in the direction of a circumference of said axis of symmetry, said information carrying areas being spaced with equal mutual distance Dica along the periphery of the cartridge in the direction of a circumference of said axis of symmetry, and said supporting means comprise two rectangular, essentially parallel, identical electrically connecting supports of height Hctm in the direction perpendicular to the axis of symmetry of the cartridge, separated by an electrically insulating volume of width Dctm between the two electrically connecting supports, and the following relations between said distances are fulfilled:

$$Hica < Dctm < 2*Hica + Dica,$$

and $$Hctm < Dica < 2*Hctm + Dctm,$$

it is ensured that the cartridge cannot be positioned in such a way that a given information carrying area has contact to two electrically connecting supports at the same time (Hica<Dctm). It is further ensured that the cartridge cannot be positioned in such a way that a given electrically connecting support has contact to two information carrying areas at the same time (Hctm<Dica). It is further ensured that the cartridge cannot be positioned in such a way that the electrically connecting supports fall entirely between two information carrying areas, in which case they would not have contact to any of the information carrying areas of the cartridge (Dica<2*Hctm+Dctm). It is further ensured that the cartridge cannot be positioned in such a way that two adjacent information carrying areas fall entirely between the electrically connecting supports, in which case the latter might not have contact to any of the information carrying areas of the cartridge (Dctm<2*Hica+Dica).

When said information carrying areas of height Hica each consist of electrically conducting and electrically insulating rectangular patches provided at said predefined positions on said cartridge according to a binary representation of said item of information, said patches having a width Wpda abut each other, and the sum of the maximum thicknesses $T_{cl}$ and $T_{il}$ of said alternating layers of electrically conducting and electrically insulating materials, respectively, constituting said electrically connecting supports, is less than the width Wpda of said patches, thus fulfilling the following relation between said distances:

$$Wpda > T_{il} + T_{cl},$$

it is ensured that each patch has contact to at least one of the conducting layers of an electrically connecting support when the cartridge is properly placed in the support.

In a preferred embodiment said alternating layers of an electrically conducting material and an electrically insulating material comprising said electrically connecting supports are made of elastic materials.

When it is made of elastic materials, it may be ensured that the support conforms to the shape of the cartridge when the cartridge is positioned in the support with a certain minimum pressure. I.e. it makes the support even more flexible and relaxes the tolerances to its conformity with the cartridge and with the contact area (e.g. pads on a PCB for connecting to a processing circuit on the PCB).

A medication delivery device having means for processing and displaying information is moreover provided by the present invention. When it is adapted for receiving a cartridge according to any one of claims 14–21, and it comprises a support according to any one of claims 22–28 for electronically reading an item of information on said cartridge, and said support transfers said item of information from said cartridge to a contact area connected with said processing means, a safe and automatic reading of an item of information on the cartridge containing the medication to be injected, infused or inhaled by a user is provided. The item of information on the cartridge may appropriately include data on the physical contents of the cartridge, the volume/amount of medication in the cartridge, the last day of recommended use of the contents, dosage information, technical data on the type of cartridge, needle, piston (if relevant), etc. The processing means may be adapted to check whether the electronically read item of information matches the expected one and to process its contents. The processing means may further be adapted to check whether the cartridge is properly inserted in the medication delivery device or whether the cartridge is a correct one by suggesting the user to check this if the electronically read item of information does not match the expected one or if no information is read at all.

An information carrier with an electronically readable item of information for a medication cartridge is moreover provided by the present invention. When said carrier is a self-adhesive electrically conducting foil adapted for being positioned on said medication cartridge, and said item of information is redundantly provided at least once by applying electrically insulating areas to predefined positions on said foil, it is ensured that a convenient and flexible means for adding an electrically readable item of information to a cartridge is provided, said means being well suited for industrial handling, optionally containing the electrically readable items of information in an optically readable form as well, e.g. as a bar code and/or in a visually intelligible form.

BRIEF DESCRIPTION OF THE DRAWINGS

The invention will be explained more fully below in connection with a preferred embodiment and with reference to the drawings in which:

FIGS. 1.a–1.f show various ways of placing information carrying areas for holding electronically readable information on a cartridge, FIGS. 2.a–2.e show various ways of laying out the electrically conducting and electrically insulating areas in predefined positions within an information carrying area, implementing a binary representation of an item of information in its true and inverted form, FIGS. 3.a–3.b show labels according to the invention with a multitude of information carrying areas containing electrically conducting and electrically insulating areas in predefined positions.

The figures are schematic and simplified for clarity, and they just show details, which are essential to the understanding of the invention, while other details are left out. In general, the reference numerals of a given drawing start with the number of that drawing, i.e. in FIG. 1, reference numerals typically have a 1 as the most significant digit (e.g. 1, 11, 102). This means on the other hand that functionally identical features occurring in different drawings have different reference numerals.

DETAILED DESCRIPTION OF EMBODIMENTS

Figure 4:
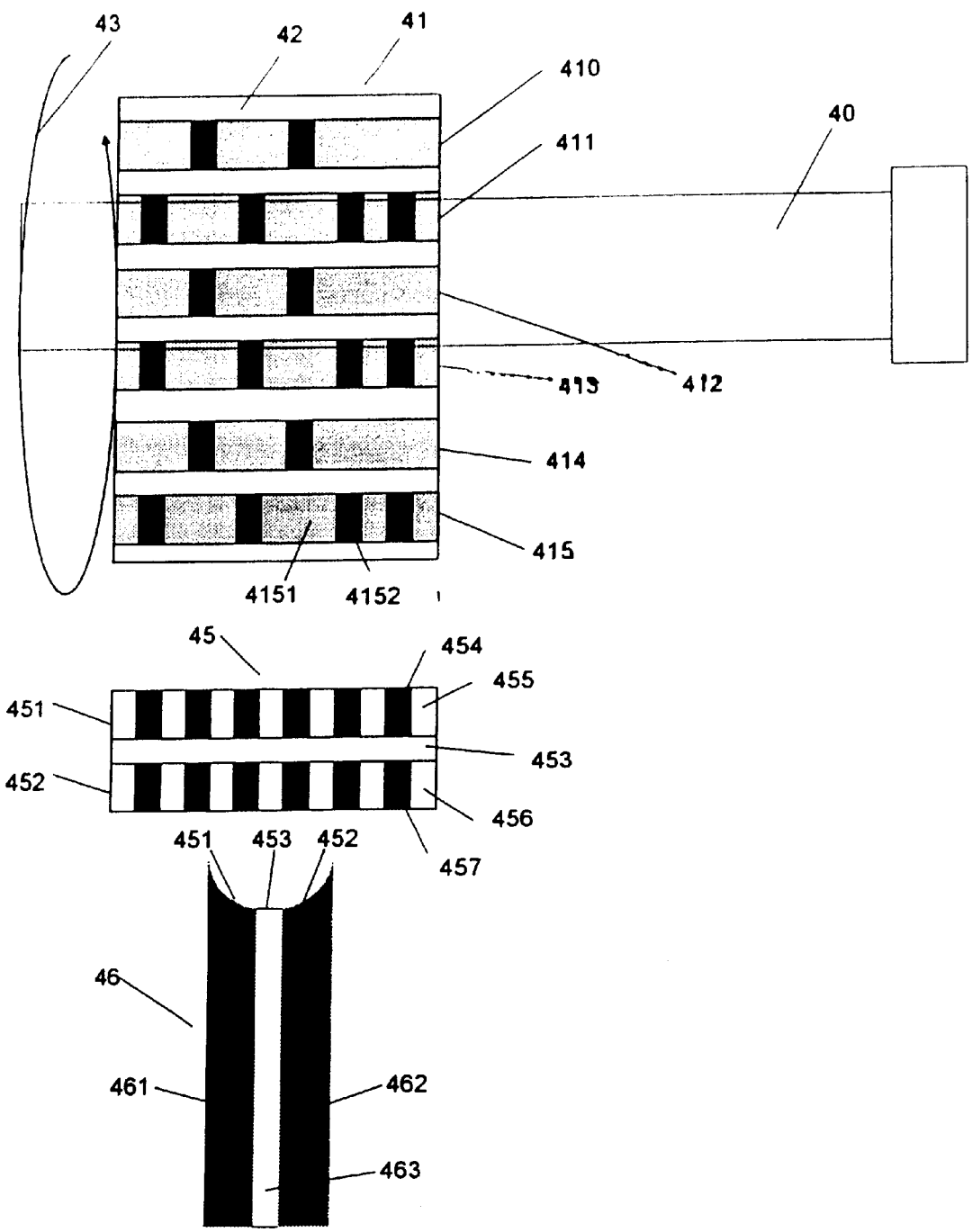
FIG. 4 shows a cartridge with a label containing an electronically readable information and a support for supporting the cartridge and for transferring the information from the cartridge to an electronic circuit, FIGS. 5.a–5.c show various geometries of an electrically connecting support according to the invention.

FIGS. 1.a–1.f show various ways of placing information carrying areas for holding electronically readable information on a cartridge. In FIGS. 1.a–1.d the information carrying areas are concentrated to one axial end of the cartridge, preferably near the lid, whereas in FIGS. 1.e–1.f the information carrying areas are concentrated to a limited radial sector of the cartridge, but extending along the full length of the cartridge.

FIGS. 1.a–1.d show a cartridge 10 with an axis of rotational symmetry 11 and information carrying areas located at one axial end of the cartridge.

FIG. 1.a shows two information carrying areas 101, 102 positioned side by side in a radial direction on the surface of the cartridge (i.e. along the periphery perpendicular to the axis of symmetry). Each information carrying area covers only a limited radial sector of the surface.

FIG. 1.b shows two information carrying areas 103, 104 positioned side by side in the axial direction on the surface of the cartridge (i.e. along the periphery parallel to the axis of symmetry). Each information carrying area covers only a limited radial sector of the surface.

FIG. 1.c shows two information carrying areas 105, 106 positioned side by side in the axial direction on the surface of the cartridge (i.e. along the periphery parallel to the axis of symmetry). Each information carrying area encircles the entire radial periphery of the cartridge.

In each of FIGS. 1.a–1.c, two information carrying areas are shown side by side. There might as well, however, be several information carrying areas located side by side in axial or radial direction.

FIG. 1.d shows information carrying areas 110, 111, 112, 113, 114 positioned side by side, evenly distributed in a radial direction on the surface of the cartridge (i.e. along the periphery perpendicular to the axis of symmetry). Each information carrying area covers only a limited radial sector of the surface. Information carrying areas 110, 111, 112, 113, 114 plus identical ones situated on the hidden part of the surface are evenly distributed on the surface of the cartridge in a radial direction, i.e. extending along the whole periphery encircling the axial direction of the cartridge.

FIGS. 1.e–1.f show a cartridge 10 with an axis of rotational symmetry 11 and information carrying areas concentrated to an area 120 corresponding to a limited radial sector 121 of the cartridge 10.

FIG. 1.e shows information carrying areas 115 and 116 side by side in axial direction and extending along the major part of the axial length of the cartridge. The information carrying areas are located within a surface area 120 corresponding to a radial sector 121.

FIG. 1.f shows information carrying areas 117 and 118 side by side in radial direction and extending along the major part of the axial length of the cartridge. The information carrying areas are located within a surface area 120 corresponding to a radial sector 121.

In FIGS. 1.e and 1.f, two information carrying areas are shown within the surface area 120. There might as well, however, be several information carrying areas located side by side in axial or radial direction.

FIGS. 2.a–2.e shows various ways of laying out the electrically conducting and electrically insulating areas in predefined positions within an information carrying area, implementing a binary representation of an item of information in its true and inverted form.

In each of FIGS. 2.a–2.e two information carrying areas containing an item of information in a true and inverted binary form, respectively, are schematically shown. Each information carrying area has a rectangular shape defining a longitudinal direction as the direction defined by its longest side. A direction is also defined by the direction perpendicular to the face between two neighboring predefined positions each containing a specific bit of information.

FIG. 2.*a* shows an embodiment with two information carrying areas 20, 21 located side by side in a direction perpendicular to the direction 205 defined by adjacent predefined positions. Each individual bit of information is implemented as a patch of electrically conducting 211 (no filling) or electrically insulating 201 (hatched) material located at a specific predefined position of the information carrying area. Neighboring patches abut each other. The structure of information carrying areas 20, 21 may e.g. be used in FIGS. 1.*a*, 1.*d*, and 1.*f*.

FIG. 2.*b* shows an embodiment with two information carrying areas 22, 23 located side by side in a direction perpendicular to the direction 225 defined by adjacent predefined positions. Each individual bit of information is implemented as a patch of electrically conducting 231 (no filling) or electrically insulating 221 (hatched) material located at a specific predefined position of the information carrying area. Neighboring patches are separated by a an 'empty' space 220, 230 of width equal to the width of each of the information carrying patches 221, 231. The 'empty' space may consist of an electrically conducting or insulating layer (as long as the pads on the PCB (cf. 763, 764 on FIG. 7) are correspondingly laid out). The structure of information carrying areas 22, 23 may e.g. be used in FIGS. 1.*a*, 1.*d*, and 1.*f*.

FIG. 2.*c* shows an embodiment with two information carrying areas 24, 25 located side by side in a direction 245 defined by adjacent predefined positions. Each individual bit of information is implemented as a patch of electrically conducting 251 (no filling) or electrically insulating 241 (hatched) material located at a specific predefined position of the information carrying area. Neighboring patches abut each other. The structure of information carrying areas 24, 25 may e.g. be used in FIGS. 1.*a*, 1.*d*, and 1.*f*.

FIG. 2.*d* shows an embodiment with two information carrying areas 26, 27 located side by side in a direction 265 defined by adjacent predefined positions. Each individual bit of information is implemented as a patch of electrically conducting 262, 271 (no filling) or electrically insulating 261, 272 (hatched) material located at a specific predefined position of the information carrying area. Neighboring patches abut each other. The structure of information carrying areas 26, 27 may e.g. be used in FIGS. 1.*b*, 1.*c*, and 1.*e*.

FIG. 2.*e* shows an embodiment with two information carrying areas 28, 29 located side by side in a direction perpendicular to the direction 285 defined by adjacent predefined positions. Each individual bit of information is implemented as a patch of electrically conducting 291 (no filling) or electrically insulating 281 (hatched) material located at a specific predefined position of the information carrying area. Neighboring patches abut each other. The structure of information carrying areas 28, 29 may e.g. be used in FIGS. 1.*b*, 1.*c*, and 1.*e*.

FIGS. 3.*a* and 3.*b* show labels according to the invention with a multitude of information carrying areas containing electrically conducting and electrically insulating areas in predefined positions.

FIG. 3.*a* shows a self-adhesive label 30 consisting of a carrier foil 31 provided with information carrying areas 310, 320, 330, 340, 350, 360, 370, each containing an item of information in its binary true or inverted form. Each information carrying area consists of a rectangular electrically conducting base, to which layers of electrically insulating rectangular patches (hatched) 312, 332, 352, 372 are added in predefined positions. The true and inverted forms appear alternatingly along the radial direction of the carrier. The binary representation of the information in information carrying area 340 is, for example, the inverse of that in 350 as indicated by corresponding bits 342 and 352, respectively, being each others inverse (342 is illustrated with no filling, indicating an electrically conducting patch, and 352 is hatched, indicating an electrically insulating patch). One predefined position 311, 321, 331, 341, 351, 361, 371 in each information carrying area 310, 320, 330, 340, 350, 360, 370, respectively is reserved for applying a power supply voltage.

FIG. 3.*b* shows a preferred embodiment of a self-adhesive label 35 consisting of an electrically conducting carrier foil 36 provided with information carrying areas 315, 325, 335, 345, 355, 365, 375, each containing an item of information in its binary true or inverted form. Each information carrying area consists of patterns of rectangular patches of electrically conducting 357, 366 (no filling) and electrically insulating patches 356, 367 (hatched) added in predefined positions. All predefined positions are illustrated for areas 355 and 365, where each electrically conducting patch (being just a predefined 'empty' position on the electrically conducting foil) is indicated by a dotted boundary line. For the other information carrying areas, only the electrically insulating patches are specifically indicated. The true and inverted forms appear alternatingly along the radial direction of the carrier. The binary representation of the information in information carrying area 355 is, for example, the inverse of that in 365 as indicated by corresponding bits (356, 366) and (357, 367), respectively, being each others inverse. A predefined area 37 of the foil is reserved for applying a power supply voltage.

FIG. 4 shows a cartridge with a label containing an electronically readable information and a support for supporting the cartridge and for transferring the information from the cartridge to an electronic circuit.

FIG. 4 shows a replaceable cartridge 40 for a pen-type injection device. The cartridge has a rotational symmetry 43. A label 41 is shown before its positioning on the surface at one axial end of the cartridge. The label consists of a self-adhesive carrier 42 with information carrying areas 410, 411, 412, 413, 414, 415, each consisting of a stripe of electrically conducting foil 4151 (light grey) with electrically insulating patches 4152 (dark grey) in predefined positions, cf. FIG. 2.*b* and FIG. 3.*a*.

FIG. 4 also shows a cross sectional view of a support 46 for receiving the cartridge corresponding to a cross section of the cartridge perpendicular to the axis of symmetry and a top view of the receiving surface 45 of the support 46 corresponding to an axial direction of the cartridge. The support 46 consists of two electrically connecting supports 461, 462 separated by an electrically insulating volume 463. The electrically connecting supports 461, 462 consist of alternating layers of electrically conducting and electrically insulating silicone rubber as shown in the 'top view' illustration by identical areas 451 and 452. The areas that are designed to receive the predefined positions 4152 (comprising an electrically insulating or conducting layer) of the information carrying areas on the cartridge are indicated by a dark grey filling, e.g. 454, 457, whereas areas with no filling, e.g. 455, 466, correspond to 'empty space' between predefined positions containing an information bit (cf. 230 in FIG. 2.*b*). The geometry of the insulating area 453, corresponding to a 'top view' cross section of insulating volume 463, is designed to match the geometry of the information carrying areas on the cartridge in such a way that two adjacent information carrying areas may be received by the support independently of the radial orientation of the cartridge, when placed in the support, cf. the discussion in connection with FIG. 6 below.

FIGS. 5.a–5.c show various geometries of an electrically connecting support according to the invention.

Common for FIGS. 5.a–5.c is that the layer thicknesses are exaggerated compared to the dimensions of the patches 51 on the information carrying areas and the pads 52 on the PCB.

FIG. 5.a shows an embodiment of an electrically connecting support 50, where the thickness $T_{il}$ 530 of the insulating layer 53 is larger than the thickness $T_{cl}$ 540 of the conducting layer 54. The patches 51 of the information carrying area are shown to be of equal width Wpda 510 and to abut each other. The pads 52 on the PCB are shown to have equal width Wcp 520 and to be evenly distributed with a distance Diacp 521 between each pad.

FIG. 5.b shows an embodiment of an electrically connecting support 50, where the thickness $T_{il}$ of the insulating layer 53 is smaller than the thickness $T_{cl}$ of the conducting layer 54.

FIG. 5.c shows an embodiment of an electrically connecting support 50, where the thickness $T_{il}$ of the insulating layer 53 equals the thickness $T_{cl}$ of the conducting layer 54.

The relation Diacp>2*$T_{cl}$ makes sure that the electrical states of adjacent information carrying patches on the cartridge are not transferred to the same pad in the contact area under the assumption that the border between adjacent patches is located at a position 'corresponding to midway between two pads'. The fulfillment of the relation Wcp>$T_{il}$+$T_{cl}$ ensures that at least one conducting layer contacts any given pad. Correspondingly, the fulfillment of the relation Wpda>$T_{il}$+$T_{cl}$ ensures that each patch has contact to at least one of the conducting layers of an electrically connecting support, when the cartridge is properly placed in the support.

In FIGS. 5.a–5.c, the information carrying patches on the cartridge are shown as abutted. This need not be the case, however. They may have any width Wpda as long as the relation Wpda>$T_{il}$+$T_{cl}$ is fulfilled to ensure that at least one conducting layer contacts any given information carrying patch.

The relations reflect the minimum distances of pads and patches and between pads and thus for given layer thicknesses determine the information density (minimum width per bit)

Figure 6:
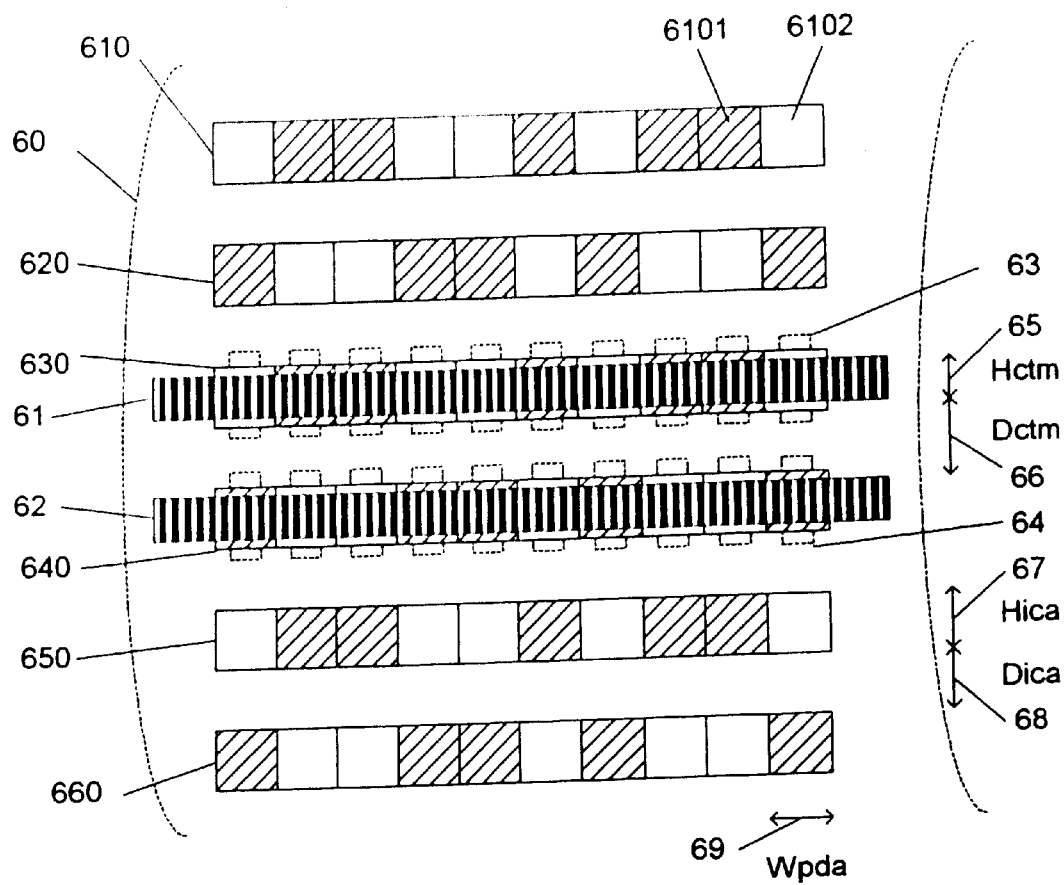
FIG. 6 shows geometries involved in reading an item of information provided a multitude of times along the periphery of a cartridge with a rotational symmetry by means of two electrically connecting supports.

FIG. 6 shows geometries involved in reading an item of information provided a multitude of times along the periphery of a cartridge with a rotational symmetry by means of two electrically connecting supports.

In FIG. 6, the electrically connecting supports 61, 62 are shown in a position where they read information from information carrying areas 630, 640, respectively, and transfer the information to groups of pads 63, 64, respectively, on a PCB. The information carrying areas 610, 620, 630, 640, 650, 660 on a label 60 carry an item of information alternatingly in a binary true and inverted form as indicated by the schematically shown individual patches of equal width Wpda 69. The patches are either electrically conducting 6102 (no filling) or electrically insulating 6101 (hatched).

The following geometric relations between the information carrying areas positioned on a cartridge and the electrically connecting supports 61, 62 of a support according to the invention for the cartridge are preferred:

$$Hica < Dctm < 2*Hica + Dica,$$

and $$Hctm < Dica < 2*Hctm + Dctm,$$

where
  Hica=Height 67 of information carrying areas
  Dica=Distance 68 between information carrying areas
  Hctm=Height 65 of electrically connecting supports
  Dctm=Distance 66 between electrically connecting supports.

Hica<Dctm ensures that the cartridge cannot be positioned in such a way that a given information carrying area has contact to two electrically connecting supports at the same time.

Hctm<Dica ensures that the cartridge cannot be positioned in such a way that a given electrically connecting support has contact to two information carrying areas at the same time.

Dica<2*Hctm+Dctm ensures that the cartridge cannot be positioned in such a way that the electrically connecting supports fall entirely between two information carrying areas, in which case they would not have contact to any of the information carrying areas of the cartridge.

Dctm<2*Hica+Dica ensures that the cartridge cannot be positioned in such a way that two adjacent information carrying areas fall entirely between the electrically connecting supports, in which case the latter might not have contact to any of the information carrying areas of the cartridge.

In a preferred embodiment, the following relation is fulfilled (in addition to the above mentioned relations between Dctm, Hctm, Dica, Hica), Dctm+Hctm=Dica+Hica, which ensures that the electrically connecting supports 61, 62 will have contact to two of the information carrying areas irrespective of the radial orientation of the cartridge in the support.

Figure 7:
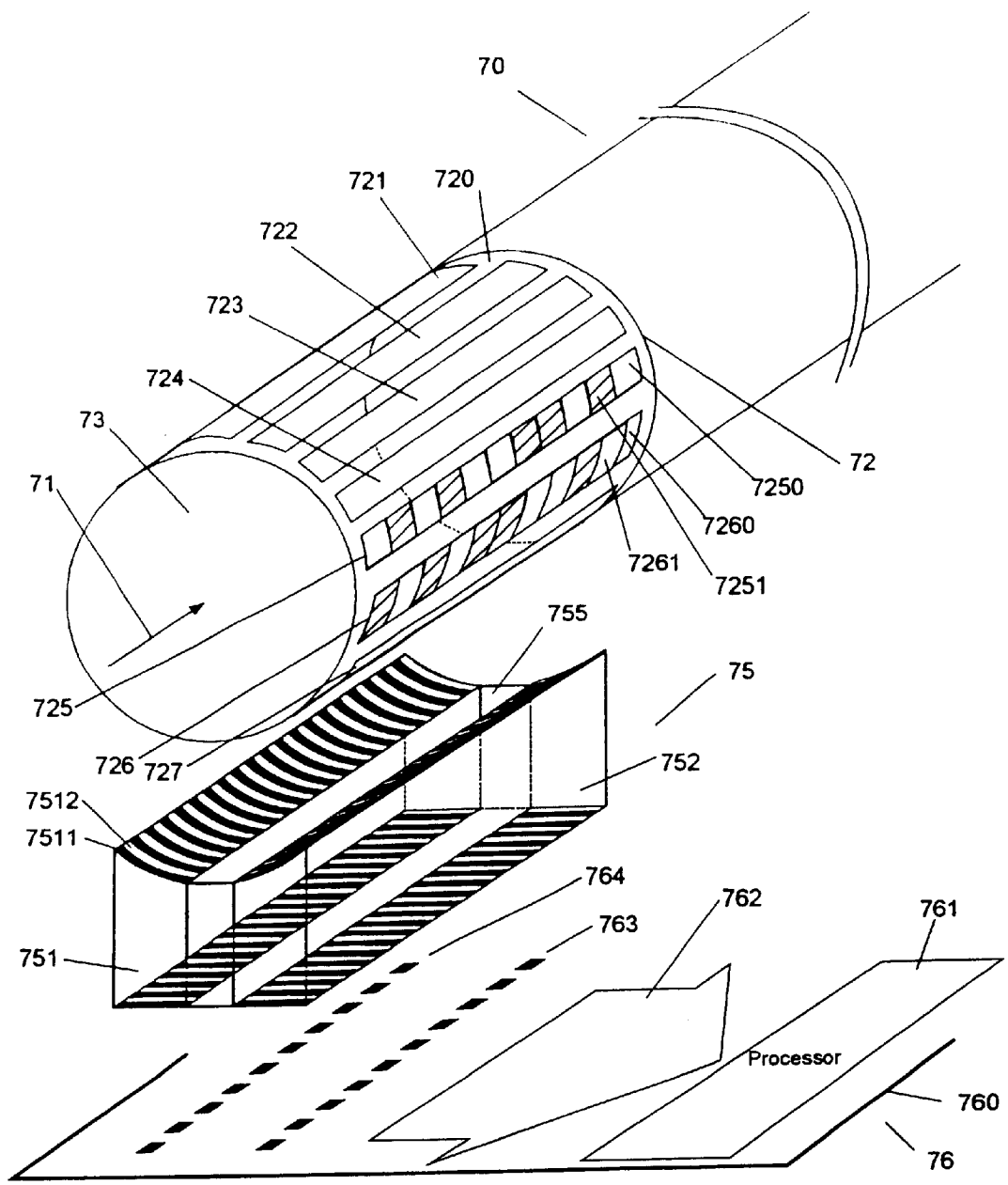
FIG. 7 shows a cartridge containing an electrically readable information according to the invention in the form of patterns of patches in the axial direction of the cartridge and a support comprising two electrically connecting supports for transferring the information to an electronic circuit, and FIGS. 8.a–8.b show an example of a cartridge and a support according to the invention comprising three electrically connecting supports made of elastic materials.

FIG. 7 shows a cartridge containing an electrically readable information according to the invention in the form of patterns of patches in the axial direction of the cartridge and a support comprising two electrically connecting supports for transferring the information to an electronic circuit.

A support according to the invention has the combined function of receiving and mechanically supporting a part of the cartridge provided with information carrying areas AND of transferring the information from these information carrying areas to an electronic circuit for further processing.

In FIG. 7, the cartridge 70 is only partially shown, as indicated by the 'broken' outline in the right-hand part of the cartridge. The cartridge possesses a rotational symmetry as indicated by the arrow 71 symbolizing the axis of symmetry. A label 72 containing information carrying areas laid out in the axial direction of the cartridge, is located on the outer surface at one axial end of the cartridge, where a lid 73, optionally in the form of a piston (e.g. when the cartridge is a replaceable medication cartridge for a medication delivery device), provides a closure of the cartridge.

The label 72 comprises an electrically conducting foil 720 having information carrying areas 721–727 extending in the axial direction of the cartridge. In FIG. 7, a multitude of information carrying areas (721–727 plus the ones situated on the hidden part of the surface) are evenly distributed on the surface of the cartridge in a radial direction (i.e. along the whole periphery encircling the axial direction of the cartridge). Each information carrying area, comprising patterns of electrically conducting 7250, 7260, 7261 and electrically insulating 7251 patches, thus only covers a limited radial sector of the surface. In the embodiment of FIG. 7, the electrically conducting 'end'-patches 7250, 7260 may be used for connecting a power supply voltage.

Each of the information carrying areas contain an item of information in the form of patterns of electrically conducting and electrically insulating areas. Each pattern represents an item of information in binary form. Each bit of information is represented by an electrically characteristic layer in a predefined position in the information carrying area. A binary one in a specific predefined position may be represented by an electrically conducting layer covering that predefined position, and a binary zero in a specific predefined position may be represented by an electrically insulating layer covering that predefined position. Alternatively, binary one may be represented by an insulating layer and binary zero by a conducting layer.

Because the foil 720 containing the information carrying areas is electrically conducting, it is only necessary to apply an electrically insulating layer (e.g. a paint) to the predefined positions representing one of the a binary states (in this embodiment 'zero').

In FIG. 7, the cartridge is shown in a position just above the support 75, which, again for illustrative purposes, is shown just above a PCB with electronic components and connecting wires 76 containing pads 763, 764 with electrical connections, symbolically indicated by an arrow 762, to a processing unit 761, e.g. a microprocessor. The support consists of one or more electrically connecting supports 751, 752 embedded in an electrically insulating material 755. The electrically connecting supports comprise alternating layers of electrically conducting 7511 and electrically insulating 7512 layers of an elastomeric material, e.g. silicone rubber with the electrically conducting layer having a concentration of carbon black sufficient for electrical conduction. Each electrically conducting layer is electrically insulated from all other electrically conducting layers, so that each electrically conducting layer in effect represents an insulated conductor. By controlling the layer thicknesses, the maximum 'density of information' in the axial direction may be controlled.

In the embodiments of FIG. 7, the support, including the electrically connecting supports, are shown to be adapted to receive the curved shape of the part of the cartridge, where the information carrying areas are located, by shaping them equivalently. This makes possible the use of non-elastic materials for the support, if convenient.

In an operating configuration, the support is placed (and optionally fastened) on the PCB 760 so that electrical contact between the electrically connecting supports 751, 752 and the pads 763, 764 is ensured. The cartridge is positioned on the support so that electrical contact between two of the information carrying areas in their full axial lengths (i.e. involving all patches of a given information carrying area representing bits of information) and the electrically connecting supports is ensured. The geometrical dimensions of the patches, layers and pads and mutual distance between adjacent information carrying areas on the cartridge and corresponding electrically connecting supports are discussed above with reference to FIGS. 5 and 6.

By applying a specific electric potential to the electrically conducting foil, this potential will be transferred from those predefined areas containing a conductive layer (i.e. in the present embodiment those predefined areas not being covered by an insulating layer) to the corresponding pads on the PCB. Via the connecting circuitry, a direct measure of the pattern of binary states of the information carrying area connected to the pads by a given electrically connecting support is presented on the inputs of the processing unit, possibly by appropriately terminating the inputs with pull-up or pull-down circuitry depending on the potential applied to the electrically conducting foil and the definition of the binary states. A specific part of the foil may be preferably reserved to the application of the electric potential (e.g. an area of the foil circumfering the cartridge and not occupied by information carrying areas, in FIG. 7 e.g. the part of the foil 720 not covered by information bits in predefined positions 721–730).

The support is only shown as having an axial length corresponding to the axial length of the corresponding information carrying areas (e.g. 725 in FIG. 7) but it may of course extend in both axial directions if appropriate for the application in question. Likewise the support is shown to cover a certain radial sector (less than 90 degrees), but it may of course cover any radial sector, including 360 degrees, if appropriate. In a preferred embodiment, the sector covered by the support is less than 180 degrees allowing a direct 'vertical' placement of the cartridge in the support (in opposition to the case of a 360 degrees support, where the cartridge has to be axially inserted).

In FIG. 7, the label containing information carrying areas is placed in one axial end of the cartridge covering only the space occupied by the axial extent of the lid/piston to ensure that a full view of the contents of the cartridge is available for inspection. Of course it might be located in any convenient position along the surface of the cartridge. Similarly, in FIG. 7, the information carrying areas extend in the axial direction of the cartridge. They might as well extend in a radial direction (as discussed in connection with FIGS. 1 and 2) or in a direction therebetween (e.g. forming one or more helixes on the surface of the cartridge), if convenient, as long as the support, including the electrically connecting supports, is adapted thereto.

The electrical connections, schematically indicated by an arrow 762, connecting the pads 763, 764 with the processing unit 761 may be a one to one parallel set of electrical connections between each pad and a corresponding input on the processor, but it may also comprise a multiplexing or coding unit to reduce the number of necessary inputs to the processing unit.

In the embodiment in FIG. 7, the support 75 comprise two electrically connecting supports 751, 752 for simultaneously reading two items of information from two information carrying areas on the cartridge. In FIG. 7 the evenly distributed information carrying areas 721–730 contain an item of information in a true binary form alternating with the information in its inverted form as indicated by the schematically illustrated patterns of electrically conducting and insulating patches in information carrying areas 725 and 726, respectively, one pattern being the inverse of the other.

The rotational symmetry of the cartridge has the benefit that it only requires the user to position the cartridge properly in a radial direction (possibly involving a slight rotation of the cartridge around its axis of symmetry) to ensure that an electrical contact between one of the information carrying areas and the electrically connecting support is present (since the positioning in an axial direction may be mechanically ensured by the receiving means for the cartridge). The control of the cartridge being correctly positioned may be in the hands of the processing unit, which, if necessary, may indicate to the user via a display or a voice interface that a corrective action is required, and which may block further use of the device, if the cartridge is not correctly positioned.

The embodiment of FIG. 7 has the further advantage of reading the information in a binary true and inverted form, which allows the safety in reading to be improved. Instead of providing the information in its true and inverted forms, the same binary representation of the item of information may be provided in all information carrying areas and read twice, which also allows an improved safety in reading.

FIGS. 8.*a*–8.*b* show an example of a cartridge and a support according to the invention comprising three electrically connecting supports made of elastic materials.

FIG. 8.*a* shows a cartridge 81 having an axis of rotational symmetry 82 being positioned just above a support 80 comprising three individual electrically connecting supports 801, 802, 803 ready for receiving the cartridge. The cartridge is provided with information carrying areas positioned on the cartridge along its radial periphery with a spacing corresponding to the geometry of the electrically connecting supports. The space between the electrically connecting supports may be filled with an insulating material (e.g. silicone rubber), not shown.

In FIG. 8.*b* the cartridge 81 is positioned in the support 80 and fixed with a slight downwards pressure indicated by the arrow 83. The support including the electrically connecting supports is made of elastic materials so that it conforms to the shape of the cartridge over the length of the support, when the cartridge is placed in the support.

The three items of information that may be simultaneously read may be identical, in which case the redundancy may be used to improve the safety in reading (by a simple majority test or by more advanced error correcting techniques).

Some preferred embodiments have been shown in the foregoing, but it should be stressed that the invention is not limited to these, but may be embodied in other ways within the subject-matter defined in the following claims.

What is claimed is:

1. A method of providing an electronically readable item of information (725) on a medication cartridge (70), the method comprising redundantly providing the item of information on the medication cartridge, wherein the item of information is provided at least once by providing a conductive foil adapted for mounting to the medication cartridge, wherein the information is provided on the foil by placing electrically insulated areas in predefined position on the foil, thereby forming on the foil electrically conducting and electrically insulating areas.

2. A method according to claim 1, characterized in that said item of information (725) is provided at least once in a binary true (725) and inverted form (726).

3. A method according to claim 2, characterized in that said medication cartridge (10) has an axis of rotational symmetry (11).

4. A method according to claim 3, characterized in that said electrically insulating or electrically conducting areas fully or partially circumfere said axis of symmetry (11), thus defining two or more information carrying areas (105, 106; 103, 104), each containing said item of information in its binary true or inverted form, on said cartridge (10).

5. A method according to claim 3, characterized in that said electrically insulating or electrically conducting areas are positioned in one or more longitudinal areas (120) stretching in the direction of said axis of symmetry (11), each longitudinal area covering only a fraction (121) of the circumference of said cartridge (10), thus defining two or more information carrying areas (115, 116; 117, 118), each containing said item of information in its binary true or inverted form, on said cartridge.

6. A method according to claim 5, characterized in that said item of information is read by applying a voltage to said electrically conducting foil (720), said voltage corresponding to the supply voltage of one of the logic levels of a digital processing circuit (761), and by connecting each predefined position on the foil electrically with inputs to said digital processing circuit (761).

7. A method according to claim 6, characterized in that said inputs to the digital processing circuit are provided with pull-up or pull-down circuitry according to which of the supply voltages of the logic levels of said digital processing circuit (761) is applied to said electrically conducting foil (720).

8. A method according to claim 7, characterized in that said inputs to the digital processing circuit (761) may be selectably provided with either pull-up or pull-down circuitry according to which of the supply voltages of the logic levels of said digital processing circuit is correspondingly selectably applied to said electrically conducting foil (720), said selection being controlled by said digital processing unit (761).

9. A method according to claim 1, characterized in that the redundant information from two or more information carrying areas (725, 726) on the cartridge (70) is transferred to a contact area (763, 764) that is connected (762) to a processing circuit (761) by supporting means (75) for the cartridge (70), the supporting means (75) being at least partially constituted by two or more electrically connecting supports (751, 752), each comprising a number of closely spaced mutually electrically insulated conductors (7511) embedded in an electrically insulating material (7512, 755) that stretches from one of the supporting surfaces of the cartridge (70) to a contact area (763, 764) for receiving and transferring the information to said processing circuit, when said cartridge (70) is positioned in said support (75).

10. A method according to claim 9, characterized in that each of said two or more electrically connecting supports (751, 752) is constituted by alternating layers of electrically conducting material (7511) of maximum thickness $T_{cl}$ and electrically insulating material (7512) of maximum thickness $T_{il}$, respectively.

11. A method according to claim 10, characterized in that said alternating layers (7511, 7512) are made of elastic materials.

* * * * *

UNITED STATES PATENT AND TRADEMARK OFFICE
CERTIFICATE OF CORRECTION

PATENT NO.        : 6,669,090 B2
APPLICATION NO. : 09/925995
DATED             : December 30, 2003
INVENTOR(S)       : Michael Eilersen It is certified that error appears in the above-identified patent and that said Letters Patent is hereby corrected as shown below:

On the title page item Assignee (73)

Change "Nordick" to --Nordisk--

Attorney (74)

Change "Yacen" to --Green--

Change "H. Bark" to --W. Bork--

Claim 4

Column 15, Line 52

Change ";" after "106" to --,--

Signed and Sealed this

Thirty-first Day of July, 2007

JON W. DUDAS
*Director of the United States Patent and Trademark Office*